US006420394B1

(12) United States Patent
Supersaxo

(10) Patent No.: US 6,420,394 B1
(45) Date of Patent: Jul. 16, 2002

(54) TOPICALLY APPLIED PHARMACEUTICAL FORMULATION

(75) Inventor: Andreas Supersaxo, Baar (CH)

(73) Assignee: Roche Consumer Health (Worldwide) SA, Geneva (CH)

( * ) Notice: Subject to any disclaimer, the term of this patent is extended or adjusted under 35 U.S.C. 154(b) by 0 days.

(21) Appl. No.: 09/057,305

(22) Filed: Apr. 8, 1998

(30) Foreign Application Priority Data

Apr. 10, 1997 (EP) .............................. 97105914

(51) Int. Cl.⁷ .................... A61K 47/00; A61K 44/30
(52) U.S. Cl. .................. 514/338; 514/561; 514/567; 514/568; 514/570; 514/571; 514/576; 514/577; 514/772; 514/772.3; 514/781; 514/944; 514/420
(58) Field of Search ................ 514/338, 420, 514/561, 567, 568, 570, 571, 576, 577, 772, 772.3, 781, 944

(56) References Cited

U.S. PATENT DOCUMENTS

| | | | | |
|---|---|---|---|---|
| 4,961,927 A | | 10/1990 | Kogure | ...................... 424/94.3 |
| 5,183,829 A | * | 2/1993 | Caldwell | ..................... 514/570 |
| 5,527,832 A | * | 6/1996 | Chi et al. | ................. 514/772.4 |
| 5,614,178 A | | 3/1997 | Bloom et al. | .................. 424/60 |
| 5,624,962 A | * | 4/1997 | Takeuchi et al. | ......... 514/772.2 |

FOREIGN PATENT DOCUMENTS

| | | |
|---|---|---|
| EP | 0 287 322 A2 | 4/1988 |
| EP | 0 733 357 A1 | 3/1996 |
| WO | 94/02176 | 2/1994 |
| WO | 95/03784 | 2/1995 |
| WO | 98/27960 | 7/1998 |

* cited by examiner

Primary Examiner—Frederick Krass
(74) Attorney, Agent, or Firm—George W. Johnston; Patricia S. Rocha Tramaloni; Arthur D. Dawson

(57) ABSTRACT

The present invention relates to a novel pharmaceutical formulation for the topical application of drugs, particularly non-steroidal anti-inflammatory drugs (NSAID's), comprising a therapeutically effective amount of a drug, sodium phosphate buffer, and, optionally, an alcoholic solvent. It has been found that by the addition of sodium phosphate buffer to such formulations, the permeation of the NSAID can be significantly improved.

7 Claims, 1 Drawing Sheet

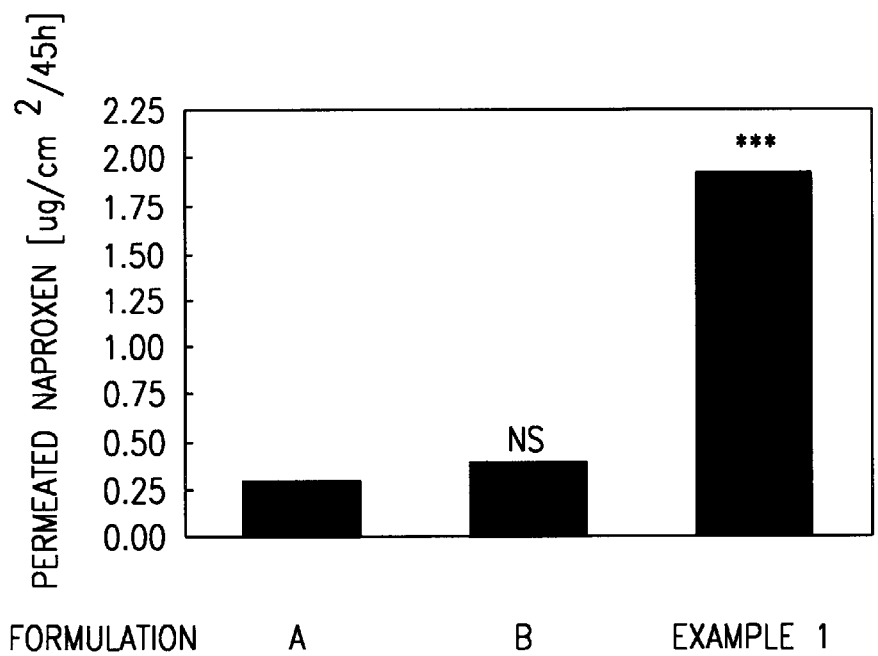

FIGURE 1. IN VITRO PERMEATION OF NAPROXEN FROM NAPROXYNGEL (A), PROPYLENE GLYCOL/ETHANOL WATER (B) AND PROPYLENE GLYCOL/ETHANOL/ SODIUM PHOSPHATE BUFFER GELS (EXAMPLE 1) ACROSS HUMAN CADAVER SKIN. EACH COLUMN REPRESENTS THE GEOMETRIC MEAN OF SEVEN EXPERIMENTS PERFORMED WITH SKIN FROM SEVEN DIFFERENT DONORS ***=P<0.005, NS= NOT SIGNIFICANT; COMPARED WITH NAPROSYNGEL, BY STUDENT'S PAIRED T-TEST.

FIG. 1

TOPICALLY APPLIED PHARMACEUTICAL FORMULATION

SUMMARY OF THE INVENTION

The present invention relates to a novel pharmaceutical formulation for the topical application of drugs, particularly non-steroidal anti-inflammatory drugs (NSAID's).

In view of adverse drug reactions associated with oral formulations, NSAID's are administered increasingly by the topical route. A prerequisite for successful topical NSAID medication is that the drug sufficiently permeates across the skin into deeper tissues such as subcutis, fasciae, tendons, ligaments and muscles to treat inflammatory degenerative and posttraumatic alterations of soft tissue structures. Hydroalcoholic formulations, e.g., ethanol/water and propylene glycol/ethanol/water are commonly used formulations for the topical application of NSAID's. In accordance with the present invention it has been found that by the addition of sodium phosphate buffer to such formulations the permeation of the NSAID can be significantly improved.

Accordingly, the invention is concerned with a formulation for topical application of drugs, particularly non-steroidal anti-inflammatory drugs (NSAID's) which formulation comprises:

(a) a therapeutically effective amount of a drug;
(b) sodium phosphate buffer; and, optionally,
(c) an alcoholic solvent.

DETAILED DESCRIPTION OF THE INVENTION

The formulations in accordance with the present invention can be present in any conventional application form. Examples of such application forms are solutions, foams, creams, ointments, lotions and gels.

The drug contained in the formulation according to the invention may be any drug that is conventionally applied topically. Drugs of primary interest for use in the present invention are NSAID's such as naproxen, ibuprofen, indomethacin, diclofenac, piroxicam or etofenamat and pharmaceutically acceptable salts thereof. A preferred NSAID for the purposes of the invention is naproxen. Additionally, any salt that is conventionally used in pharmaceutical preparations for NSAID's can be used. Examples of such salts are alkali metal salts such as sodium and potassium salts, and substituted ammonium salts such as salts with alkylamines and hydroxyalkylamines, e.g. diethylamine and triethanolamine. The molarity of the sodium phosphate buffer is suitably in the range of from about 10 to 300 mM, preferably about 100 to about 200 mM. The pH of the buffer solution is preferably between 5 and 7.5, more preferably 6.0 to 7.5. Most preferred is pH 6.0. The alcoholic solvent can be any such solvent conventionally used in topical formulations. Preferred alcoholic solvents are ethanol, isopropanol, propylene glycol and mixtures thereof. Another example of an alcoholic solvent is glycerol. Preferred alcoholic solvents are mixtures of ethanol and propylene glycol in a ratio of 3:1 parts by weight.

If a gel formulation is desired, any gel forming agent commonly used in pharmaceutical gel formulations can be used. Examples of gel forming agents are cellulose derivatives such as methyl cellulose, hydroxyethyl cellulose, carboxymethyl cellulose; vinyl polymers such as polyvinyl alcohols, polyvinyl pyrrolidones; and polyacryl derivatives such as Carbopol. Further gelling agents that can be used for the compositions in accordance with the invention are pectins, gums, such gum arabic and tragacanth, alginates, carrageenates, agar and gelatine. The preferred gelling agent used in the present invention is hydroxypropylmethyl cellulose (HPMC). Further, the gel formulation of this invention may also contain auxiliary agents commonly used in such formulations such as preservatives, antioxidants, stabilizers, colorants and perfumes.

The amount of active ingredient present in the formulations of the present invention is generally the same as in corresponding conventional formulations. If the drug, i.e. the active ingredient, is a NSAID its amount may vary, e.g., from about 0.1 to about 10 g of NSAID per 100 g of finished formulation, preferably 0.5–2.5 g, most preferably about 1 g per 100 g of finished formulation. The amount of sodium phosphate buffer may vary from about 30 to about 90–99 g, preferably about 30 to about 70 g of a 100–200 mM solution per 100 g of finished formulation. The amount of alcoholic solvent is suitably from about 5 to about 70 g per 100 g of finished formulation. In a preferred aspect of the invention the alcoholic solvent comprises about 20 to about 40 g of ethanol and about 5 to about 30 g of propylene glycol. In gel formulations the amount of gelling agent sufficient to obtain a gel formulation having adequate viscosity for application on the skin depends on the particular gelling agent or agents used and the desired viscosity of the finished gel formulation and can be determined by the pharmaceutical formulation expert depending on the individual requirements.

The formulations in accordance with the present invention can be prepared in a conventional manner. For example, the drug, e.g., a NSAID is dissolved in the aqueous buffer solution and, optionally, alcoholic cosolvents. The obtained solution may then be gelled by adding a gelling agent, e.g., hydroxyethylcellulose or hydroxypropylmethyl cellulose.

BRIEF DESCRIPTION OF THE DRAWING

FIG. 1 shows permeation studies as described in Example 8.

The following Examples illustrate the invention:

EXAMPLE 1

A gel was prepared from the following constituents:

| Constituent | [gram] |
| --- | --- |
| Naproxen sodium | 1.1 |
| Ethanol | 30.0 |
| Propylene glycol | 10.0 |
| Aqueous sodium phosphate buffer pH 6.0 200 mM | 50.0 |
| Hydroxyethyl cellulose | 1.6 |
| Water q.s. ad | 100.0 |

EXAMPLE 2

A gel was prepared from the following constituents:

| Constituent | [gram] |
| --- | --- |
| Naproxen sodium | 1.1 |
| Ethanol | 30.0 |
| Propylene glycol | 10.0 |
| Aqueous sodium phosphate buffer pH 6.0 100 mM | 50.0 |

-continued

| Constituent | [gram] |
| --- | --- |
| Hydroxypropylmethyl cellulose | 2.5 |
| Water q.s. ad | 100.0 |

EXAMPLE 3
Gel was prepared from the following constituents:

| Constituent | [gram] |
| --- | --- |
| Naproxen (free acid) | 1.0 |
| Triethanolamine | 0.65 |
| Ethanol | 30.0 |
| Propylene glycol | 10.0 |
| Aqueous sodium phosphate buffer pH 6.0 200 mM | 50.0 |
| Hydroxyethyl cellulose | 1.6 |
| Water q.s. ad | 100.0 |

EXAMPLE 4
A gel was prepared from the following constituents:

| Constituent | [gram] |
| --- | --- |
| Naproxen sodium | 2.74 |
| Ethanol | 30.0 |
| Propylene glycol | 10.0 |
| Aqueous sodium phosphate buffer pH 6.0 200 mM | 50.0 |
| Hydroxyethyl cellulose | 1.6 |
| Water q.s. ad | 100.0 |

EXAMPLE 5
A gel was prepared from the following constituents:

| Constituent | [gram] |
| --- | --- |
| Naproxen sodium | 5.5 |
| Ethanol | 30.0 |
| Propylene glycol | 10.0 |
| Aqueous sodium phosphate buffer pH 6.0 200 mM | 50.0 |
| Hydroxyethyl cellulose | 1.6 |
| Water q.s. ad | 100.0 |

EXAMPLE 6
A gel was prepared from the following constituents:

| Constituent | [gram] |
| --- | --- |
| Naproxen sodium | 1.1 |
| Ethanol | 30.0 |
| Propylene glycol | 10.0 |
| Aqueous sodium phosphate buffer pH 6.0 100 mM | 50.0 |
| Hydroxyethyl cellulose | 1.6 |
| Water q.s. ad | 100.0 |

EXAMPLE 7
A gel can be prepared from the following constituents:

| Constituent | [gram] |
| --- | --- |
| Naproxen sodium | 1.1 |
| Aqueous sodium phosphate buffer pH 7.25 100 mM | 50.0 |
| Hydroxyethyl cellulose | 1.6 |
| Water q.s. ad | 100.0 |

EXAMPLE 8

Skin Permeation Studies

Skin permeation of naproxen from formulations in accordance with Example 1 of the invention; unbuffered formulation in accordance with Example 1 of the invention (Formulation B); and from a prior art formulation (NaprosynGEL™), (Formulation A) was measured. Formulation A and B and Example 1 were prepared having the composition given below:

| Formulation | A [gram] | B | Example 1 |
| --- | --- | --- | --- |
| Naproxen (free acid) | 10.0 | — | — |
| Naproxen sodium | — | 1.1 | 1.1 |
| Triethanolamine | 13.0 | — | — |
| Ethanol | 30.0 | 30.0 | 30.0 |
| Propylene glycol | — | 10.0 | 10.0 |
| Hydroxyethyl cellulose | — | 1.6 | 1.6 |
| Carbomer 940 | 2 | — | — |
| Sodium metabisulfite | 0.1 | — | — |
| Rose fragrance | 0.03 | — | — |
| Aqueous sodium phospate buffer pH 6.0 200 mM | | | 50 |
| Water q.s. ad | 100.0 | 100.0 | 100.0 |

Skin samples of abdominal skins from human cadavers were dermatomed (0.38 mm) and freezed at −80° C. At the day of experiment the skin samples were thawed and mounted in Franz-type diffusion cells with a diffusional cross-sectional are of 1 cm and a receptor chamber volume of 5 ml. The receptor compartments, equipped with magnetic stirring bars, were filled with 1 mM phosphated buffered saline, pH 7.4. The diffusion cells were then transferred into a heating box thermostated at 32° C. Following an equilibration period of 3–4 h, 5 mg/cm$^2$ of the test formulations were applied to epidermal surfaces using micropipets. After 45 h incubation under non-occluded conditions at 32° C. the receptor solutions were withdrawn and naproxen concentrations were measured by HPLC. Results are presented in FIG. 1.

What is claimed is:
1. A gel formulation comprising per 100 g of formulation:
 (a) about 0.1 to about 10 g of a non-steroidal anti-inflammatory drug;
 (b) about 30 to about 70 g of 10 to 300 mM sodium phosphate buffer pH 5 to 7.5;
 (c) about 20 to about 40 g of an alcoholic solvent selected from the group consisting of ethanol, isopropanol and a mixture thereof;
 (d) about 5 to about 30 g of propylene glycol; and

(e) at least one gelling agent in an amount sufficient to obtain a gel formulation having adequate viscosity for application to the skin.

2. A gel formulation as in claim 1 wherein the gelling agent is hydroxypropylmethyl cellulose.

3. A gel formulation as in claim 1 wherein the non-steroidal anti-inflammatory drug is naproxen sodium.

4. A gel formulation as in claim 2 wherein the non-steroidal anti-inflammatory drug is naproxen sodium.

5. A gel formulation of claim 3 wherein the non-steroidal anti-inflammatory drug is about 1% naproxen sodium.

6. A gel formulation of claim 4 wherein the non-steroidal anti-inflammatory drug is about 1% naproxen sodium.

7. A gel formulation comprising per 100 g of formulation:

(a) about 0.1 to about 10 g of a non-steroidal anti-inflammatory drug;

(b) about 30 to about 70 g of 10 to 300 mM sodium phosphate buffer pH 5 to 7.5;

(c) about 20 to about 40 g of an alcoholic solvent selected from the group consisting of ethanol, isopropanol and a mixture thereof; and (d) at least one gelling agent in an amount sufficient to obtain a gel formulation having adequate viscosity for application to the skin.

* * * * *